(12) United States Patent
Kayser et al.

(10) Patent No.: US 11,142,494 B2
(45) Date of Patent: Oct. 12, 2021

(54) COMPOUND COMPRISING CERTAIN LEVEL OF BIO-BASED CARBON

(71) Applicant: Clariant International Ltd., Muttenz (CH)

(72) Inventors: Christoph Kayser, Mainz (DE); Gundula Starkulla, Mainz (DE); Dirk Fischer, Hahnheim (DE); Paul Kaufmann, Hochheim (DE); Michael Schäfer, Gründau-Rothenbergen (DE); Katharina Götz, Munich (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 16/311,162

(22) PCT Filed: Jun. 19, 2017

(86) PCT No.: PCT/EP2017/064977
§ 371 (c)(1),
(2) Date: Dec. 18, 2018

(87) PCT Pub. No.: WO2017/220512
PCT Pub. Date: Dec. 28, 2017

(65) Prior Publication Data
US 2019/0241509 A1 Aug. 8, 2019

(30) Foreign Application Priority Data

Jun. 20, 2016 (EP) .................................. 16175218

(51) Int. Cl.
| | | |
|---|---|---|
| *C07C 309/15* | (2006.01) | |
| *C08F 20/58* | (2006.01) | |
| *C08F 10/00* | (2006.01) | |
| *C07C 303/06* | (2006.01) | |
| *C07C 303/44* | (2006.01) | |

(52) U.S. Cl.
CPC .......... *C07C 309/15* (2013.01); *C07C 303/06* (2013.01); *C08F 10/00* (2013.01); *C08F 20/58* (2013.01); *C07C 303/44* (2013.01)

(58) Field of Classification Search
CPC ... C07C 309/15; C07C 303/06; C07C 303/44; C08F 20/58; C08F 10/00
See application file for complete search history.

(56) References Cited

U.S. PATENT DOCUMENTS

| | | | |
|---|---|---|---|
| 629,733 A | 7/1899 | Waterman | |
| 2,614,989 A | 10/1952 | Hunter | |
| 2,809,971 A | 10/1957 | Bernstein | |
| 2,865,876 A | 12/1958 | Scott, Jr. | |
| 2,904,580 A | 9/1959 | Idol, Jr. | |
| 2,905,565 A | 9/1959 | Dietz | |
| 3,052,628 A | 9/1962 | Stanberry, Jr. | |
| 3,236,733 A | 2/1966 | Karsten | |
| 3,509,113 A | 4/1970 | Monagle | |
| 3,544,597 A * | 12/1970 | Killam | ...................... C09K 8/22 |
| | | | 549/63 |
| 3,753,196 A | 8/1973 | Kurtz | |
| 3,761,418 A | 9/1973 | Parran | |
| 3,937,721 A * | 2/1976 | Schroeck | .............. C07C 303/26 |
| | | | 558/49 |
| 3,960,918 A * | 6/1976 | Schroeck | .............. C07C 309/63 |
| | | | 558/49 |
| 4,015,991 A | 4/1977 | Persinski | |
| 4,138,430 A | 2/1979 | Stiles | |
| 4,323,683 A | 4/1982 | Bolich, Jr. | |
| 4,342,653 A | 8/1982 | Halverson | |
| 4,345,080 A | 8/1982 | Bolich, Jr. | |
| 4,379,753 A | 4/1983 | Bolich, Jr. | |
| 4,470,982 A | 9/1984 | Winkler | |
| 4,487,864 A | 12/1984 | Bermudez | |
| 4,555,269 A | 11/1985 | Rao | |
| 4,655,943 A * | 4/1987 | Elmquist | ................... C08J 3/03 |
| | | | 166/308.5 |

(Continued)

FOREIGN PATENT DOCUMENTS

| | | |
|---|---|---|
| CN | 101066940 A | 11/2007 |
| CN | 101636381 A | 1/2010 |

(Continued)

OTHER PUBLICATIONS

Le Nôtre et al, Green Chemistry, Biobased synthesis of acrylonitrile from glutamic acid, 2011, 13, pp. 807-809. (Year: 2011).*
ASTM International, ASTM D6866-12, Standard Test Methods for Determining the Biobased Content of Solid, Liquid, and Gaseous Samples Using Radiocarbon Analysis (2012) (Year: 2012).*
Adhikary et al, Synthesis, characterization, and application of amylopectin-graft-poly(AM-co-AMPS), Journal of Applied Polymer Science (2012), 126(S1), 6 pages.
Babu, R. P. et al., "Current progress on bio-based polymers and their future trends", Progress in Biomaterials 2013, 2(8), 1-16. (Year: 2013).
CTFA Cosmetic Ingredient Dictionary, 3 pages.
CTFA Cosmetic Ingredient Handbook, Second Edition, 1992, 2 pages.

(Continued)

*Primary Examiner* — Alexander R Pagano
(74) *Attorney, Agent, or Firm* — Tod A. Waldrop

(57) ABSTRACT

The present invention relates to a compound according to Formula (3), wherein the compound comprises from 28 wt. % to 100 wt. % bio-based carbon content, relative to the total mass of carbon in the compound, measured according to standard ASTM D6866-12, Method B;

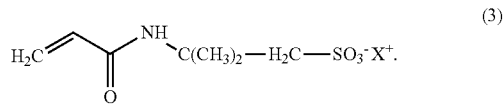

(3)

and wherein $X^+$ is a proton. The present invention also relates to a polymer obtained by polymerising at least one of compound according to Formula (3), in addition to processes and uses related thereto.

20 Claims, No Drawings

(56) References Cited

U.S. PATENT DOCUMENTS

| | | | |
|---|---|---|---|
| 4,669,920 A | 6/1987 | Dymond | |
| 4,703,801 A | 11/1987 | Fry | |
| 4,722,958 A | 2/1988 | Sauer | |
| 4,800,071 A | 1/1989 | Kaesler | |
| 4,931,489 A | 6/1990 | Kucera | |
| 5,025,040 A | 6/1991 | Crema | |
| 5,104,646 A | 4/1992 | Bolich, Jr. | |
| 5,194,639 A | 3/1993 | Connor | |
| 5,331,021 A | 7/1994 | Ahmed | |
| 5,472,051 A | 12/1995 | Brothers | |
| 5,510,049 A | 4/1996 | Connor | |
| 5,792,828 A * | 8/1998 | Quinn | C07C 303/32 525/328.5 |
| 6,277,900 B1 | 8/2001 | Oswald | |
| 6,297,337 B1 | 10/2001 | Marchant | |
| 6,437,068 B2 | 8/2002 | Loeffler | |
| 6,683,144 B2 | 1/2004 | Loeffler | |
| 6,891,009 B2 | 5/2005 | Loeffler | |
| 7,208,556 B2 | 4/2007 | Loeffler | |
| 8,420,214 B2 | 4/2013 | Kavanagh | |
| 8,629,224 B2 | 1/2014 | Loeffler | |
| 2003/0064044 A1 | 4/2003 | Chen | |
| 2004/0228809 A1 | 11/2004 | Birkel | |
| 2005/0003984 A1 | 1/2005 | Himmrich | |
| 2006/0019835 A1 | 1/2006 | Kayser | |
| 2007/0100102 A1 | 5/2007 | Fenchl | |
| 2010/0048850 A1 | 2/2010 | Dubois | |
| 2010/0274048 A1 | 10/2010 | Wakayama | |
| 2010/0278763 A1 | 11/2010 | Loeffler | |
| 2010/0311904 A1 | 12/2010 | Chambers | |
| 2010/0331904 A1 | 12/2010 | Warren | |
| 2011/0110878 A1 | 5/2011 | Knappe | |
| 2011/0136718 A1 | 6/2011 | Rodrigues | |
| 2011/0318515 A1 | 12/2011 | Dubois | |
| 2012/0039819 A1 | 2/2012 | Nakatani | |
| 2012/0100084 A1 | 4/2012 | Peter | |
| 2012/0138299 A1 | 6/2012 | Joseph | |
| 2013/0043384 A1 * | 2/2013 | Matsumoto | B01J 20/261 250/282 |
| 2013/0129652 A1 | 5/2013 | Blin | |
| 2014/0086854 A1 | 3/2014 | Klug | |
| 2014/0127147 A1 | 5/2014 | Klug | |
| 2014/0128513 A1 | 5/2014 | Carlson | |
| 2014/0154758 A1 | 6/2014 | Dubois | |
| 2015/0239803 A1 * | 8/2015 | Sun | C07C 2/867 526/337 |
| 2015/0329877 A1 | 11/2015 | Bockrath | |
| 2018/0171051 A1 * | 6/2018 | Junk | C08L 33/12 |
| 2018/0171207 A1 | 6/2018 | Fischer | |
| 2019/0058195 A1 * | 2/2019 | Hanasaki | H01M 4/0404 |
| 2019/0202737 A1 * | 7/2019 | Hesselbarth | C04B 14/106 |
| 2019/0241509 A1 | 8/2019 | Kayser | |
| 2019/0338060 A1 | 11/2019 | Fischer | |
| 2019/0359735 A1 | 11/2019 | Fischer | |
| 2020/0009041 A1 | 1/2020 | Fischer | |
| 2020/0010598 A1 | 1/2020 | Fischer | |
| 2020/0017618 A1 | 1/2020 | Fischer | |
| 2020/0017619 A1 | 1/2020 | Fischer | |
| 2020/0078287 A1 | 3/2020 | Fischer | |
| 2020/0095356 A1 | 3/2020 | Fischer | |
| 2020/0270506 A1 | 8/2020 | Fischer | |

FOREIGN PATENT DOCUMENTS

| | | |
|---|---|---|
| CN | 102351744 A | 2/2012 |
| CN | 102361894 A | 2/2012 |
| CN | 102952044 A | 3/2013 |
| CN | 103492437 A | 1/2014 |
| CN | 103819614 | 5/2014 |
| CN | 104204080 A | 12/2014 |
| CN | 104884628 A | 9/2015 |
| CN | 105694403 A | 6/2016 |
| DE | 2655891 | 6/1977 |
| EP | 0116671 | 8/1984 |
| EP | 0157055 | 10/1985 |
| EP | 0217608 | 4/1987 |
| EP | 0244981 | 11/1987 |
| EP | 0550637 | 7/1993 |
| EP | 0750899 | 1/1997 |
| EP | 0816403 | 1/1998 |
| EP | 1045869 | 10/2000 |
| EP | 1084696 | 3/2001 |
| EP | 1351654 A1 | 10/2003 |
| EP | 2105127 A1 | 9/2009 |
| EP | 2166060 | 3/2010 |
| JP | 2008084852 A | 4/2008 |
| JP | 2010519191 A | 6/2010 |
| JP | 2011506703 A | 3/2011 |
| WO | 9206154 | 4/1992 |
| WO | 9507340 | 3/1995 |
| WO | 9800094 | 1/1998 |
| WO | 9924549 | 5/1999 |
| WO | 9926991 | 6/1999 |
| WO | 9966017 | 12/1999 |
| WO | 0226925 | 4/2002 |
| WO | 2009063120 A1 | 5/2009 |
| WO | 2009072480 A | 6/2009 |
| WO | 2010092875 A1 | 8/2010 |
| WO | 2012084977 A1 | 6/2012 |
| WO | 2012113671 | 8/2012 |
| WO | 2013017262 A1 | 2/2013 |
| WO | 2013113938 A1 | 8/2013 |
| WO | 2013120636 A1 | 8/2013 |
| WO | 2013178668 | 12/2013 |
| WO | 2013178700 | 12/2013 |
| WO | 2014004616 | 1/2014 |
| WO | 2014086780 A2 | 6/2014 |
| WO | 2015034948 | 3/2015 |
| WO | 2016042011 | 3/2016 |
| WO | 2017220512 | 12/2017 |

OTHER PUBLICATIONS

De Jong et al, "Product developments in the bio-based chemicals arena", Biofuels, Bioprod. Bioref. 6:606-624 (2012).

EP1351654B1—Google English Translation (Year: 2003), 19 pages.

International Preliminary Report on Patentability for PCT/EP2017/064977, dated Dec. 25, 2018, 7 pages.

International Search Report for PCT/EP2017/06477, dated Aug. 29, 2017, 2 pages.

Pourjavadi et al, "Modified Carrageenan. 4. Synthesis and Swelling Behavior of Crosslinked C-g-AMPS Superabsorbent Hydrogel with Antisalt and pH-Responsiveness Properties", Journal of Applied Polymer Science, vol. 98, 255-263 (2005).

Rana, V. et al, "Carbohydrate Polymers", 83 (2011) 1031-1047.

Renae Canterbery Pepe et al., International Cosmetic Ingredient Dictionary and Handbook, 9th Edition, 2002, vol. 4, Published by the Cosmetic, Toiletry, and Fragrance Association, 3 pages.

Srivastava et al, "Graft copolymerization of 2-Acrylamideo-2-methyl-1-propane sulphonic acid onto xanthan gum by ascorbic/bromate redox pair," PMSE Preprints (2004), 90, pp. 291-292.

Srivastava et al, Modification of natural polymer via free radical graft copolymerization of 2 acrylamideo-2-methyl-1-propane sulfonic acid in aqueous media and study of swelling and metal ion sorption behaviour, Journal of Applied Polymer Science (2009), 114(3), 1426-1434.

Anonymous, "Bio-based material—Wikipedia, the free encyclopedia", (Mar. 12, 2015), URL: https://en.wikipedia.org/wiki/Bio-based_material, (Sep. 1, 2016), XP055299147.

Bernd Tieke, "Makromolekulare Chemie Chapter 3", ISBN 10:3527313796.

Bernd Tieke, "Makromolekulare Chemie: Eine Einführung", Wiley-VCH, 2. vollständig überarbeitete und erweiterte Auflage (3. Nachdruck 2010) ISBN-13: 978 3-527-31379-2, p. 259-261.

Bianca et al., "Fermentative production of isobutene", Appl Microbiol Biotechnol (2012) 93:1377-1387.

Dräger-Röhrchen & CMS-Handbuch, 17. Auflage, März 2015, 9 pages.

(56) References Cited

OTHER PUBLICATIONS

George Odian, "Principles of Polymerization", Third Edition, Wiley-Interscience, New York, in chapter 1-4, p. 19 to 24, ISBN 0-471-61020-8, Aug. 1992.
International Search Report for App. No. PCT/EP2017/081415, dated Jan. 16, 2018, 3 pages.
International Search Report for App. No. PCT/EP2017/081417, dated Apr. 4, 2018, 2 pages.
International Search Report for App. No. PCT/EP2017/081667, dated Jan. 23, 2018, 3 pages.
International Search Report for App. No. PCT/EP2017/081681, dated Apr. 11, 2018, 3 pages.
International Search Report for PCT/EP2017/081665, dated Jan. 23, 2018, 2 pages.
International Search Report for PCT/EP2017/081666, dated Jan. 23, 2018, 2 pages.
Kourosh Kabiri et al: "Chitosan-modified nanoclay-poly(AMPS) nanocomposite hydrogels with improved gel strength", Polymer International, vol. 58, No. 11, Sep. 10, 2009 (Sep. 10, 2009), pp. 1252-1259, XP055379190.
M. A. Bañares, M. O. Guerrero-Pérez, "Appl. Catal. B: Environmental", 148-149 (2013) 601-603.
M. O. Guerrero-Pérez, M. A. Bañares, "New Reaction: Conversion of Glycerol into Acrylonitrile", ChemSusChem 1 (2008) 511-513.
M. O. Guerrero-Péreza and M. A. Bañares, "Metrics of acrylonitrile: From biomass vs. petrochemical route", Catalysis Today 239 (2015) 25-30.
Machine Translation of AOI Keigo, et al, Bio-based Polymers Seni Gakkaishi, 2010, vol. 66 No. 4, p. 124-128.
Machine Translation of Netsu Sokutei, 2012, 39(4), p. 143-150.
Masao Kunioka, "Measurement Methods of Biobased Carbon Content for Biomass-Based Chemicals and Plastics", Radioisotopes, 62, 901-925 (2013).
Mithilesh Yadav et al: "Superabsorbent nanocomposite (alginate-g-PAMPS/MMT): Synthesis, characterization and swelling behavior", Carbohydrate Polymers, Applied Science Publishers, Ltd. Barking, GB, vol. 90, No. 1, May 4, 2012 (May 4, 2012), pp. 165-173, XP028432003.

\* cited by examiner

COMPOUND COMPRISING CERTAIN LEVEL OF BIO-BASED CARBON

FIELD OF THE INVENTION

The present invention relates to a compound having a certain bio-based carbon content as well as to a polymer obtained by polymerizing at least one of said compound, in addition to processes and uses related thereto.

BACKGROUND OF THE INVENTION

Many materials employed for use as thickeners or rheology modifiers are traditionally derived from crude oil. Environmental, economic and sustainability questions are restricting the use of products derived from this limited resource: synthetic surfactants, for example, have been blamed for environmental incidents, particularly vis-à-vis aquatic problems in rivers and lakes. Therefore, there is a desire to identify more sustainable and biodegradable, yet gentle and effective materials. Indeed, consumers are very interested in "natural" products including products with a high percentage of "natural" compounds and/or compounds that are derived from renewable materials. Consumers perceive compounds derived from natural materials to be gentler and more environmentally friendly. Recent industrial developments in "bio-based" chemicals are summarised, for example, in de Jong et al, "Product developments in the bio-based chemicals arena", Biofuels, Bioprod. Bioref. 6:606-624 (2012).

Recently, classical monomers such as ethylene, acrylic acid or methyl methacrylate have been disclosed as being produced with renewable raw materials. US2014/0154758 (Arkema) discloses the preparation of methyl methacrylate wherein the method comprises the use of acetone cyanohydrin as a raw material, said acetone cyanohydrin being obtained by condensing cyanohydric acid in acetone, and the methyl methacrylate is prepared using a process involving the addition of methanol. Acetone and methanol can be sourced from renewable feedstock. DE 2,655,891 (DU PONT) discloses the oxidation from 1-propanol to acrylates. U.S. Pat. No. 4,138,430 (DU PONT) discloses the ammoxidation of 1-propanol to form acrylonitrile.

Different synthetic routes for the synthesis of bio-based acrylonitrile are described by M. Olga Guerrero-Péreza and Miguel A. Bañares in Catalysis Today 239 (2015) 25-30. The process for the direct production of acrylonitrile from glycerol was described recently by M. O. Guerrero-Pérez, M. A. Bañares, ChemSusChem 1 (2008) 511 and by M. A. Bañares, M. O. Guerrero-Pérez, Appl. Catal. B (2013), as well as in US20100048850A1 (Arkema) and WO2009063120A1 (CONSEJO SUPERIOR DE INVESTIGACIONES CIENTIFICAS).

Bio-based propylene can directly been used in the so-called SOHIO process to form acrylonitrile. U.S. Pat. No. 2,904,580 (STANDARD OIL CO) describes the ammoxidation of propylene according to the so-called SOHIO process.

WO2014086780 (Global Bioenergies) discloses a fermentation method for several olefins including propene and isobutene. As seen before propene can be used as a raw material for the ammoxidation to acrylonitrile. Isobutene is an important raw material for polyisobutene rubbers and other downstream products such as tert.-butanol, iso-octanol, branched alkanes or branched alcohols.

WO2016/042011 (Global Bioenergies) describes an enzymatic method for the production of isobutene from 3-methylcrotonyl-CoA. WO2014/004616 (Gevo Inc) discloses the synthesis of isobutanol by recombinant yeast microorganisms. The catalytic dehydration leads to isobutene.

WO2015/034948 (MYRIANT CORP) describes the synthesis of bio-based acrylic acid by dehydration of 1,3-propandiol and subsequent oxidation of the allylic alcohol.

Nevertheless, the availability of more renewable building blocks for polymers suitable for use as thickening agents is highly limited. Furthermore, there is a need for thickening agents that are not only more renewable, but also provide excellent performance. There is a need, therefore, for providing building blocks for polymers that can provide the excellent performance of modern polymers yet from more sustainable sources.

SUMMARY OF THE INVENTION

In a first aspect, the present invention relates to a compound according to Formula (3), wherein the compound comprises from 28 wt. % to 100 wt. % bio-based carbon content, relative to the total mass of carbon in the compound, measured according to standard ASTM D6866-12, Method B;

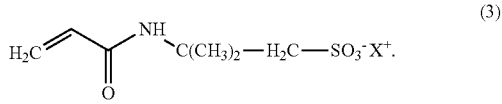

(3)

and wherein $X^+$ is a proton.

Other aspects relate to compounds, polymers, processes and uses related to the compound of the first aspect.

DETAILED DESCRIPTION OF THE INVENTION

Definitions and General

In this document, including in all embodiments of all aspects of the present invention, the following definitions apply unless specifically stated otherwise. All percentages are by weight (w/w) of the total composition. "wt.-%" means percentage by weight; "vol.-%" means percentage by volume; "mol.-%" means percentage by mole. All ratios are weight ratios. References to 'parts' e.g. a mixture of 1 part X and 3 parts Y, is a ratio by weight. "QS" or "QSP" means sufficient quantity for 100% or for 100 g. +/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 23° C. and at ambient conditions, where "ambient conditions" means at 1 atmosphere (atm) of pressure and at 50% relative humidity. "Relative humidity" refers to the ratio (stated as a percent) of the moisture content of air compared to the saturated moisture level at the same temperature and pressure. Relative humidity can be measured with a hygrometer, in particular with a probe hygrometer from VWR International. Herein "min" means "minute" or "minutes". Herein "mol" means mole. Herein "g" following a number means "gram" or "grams". "Ex." means "example". All amounts as they pertain to listed ingredients are based on the active level (solids') and do not include carriers or by-products that may be included in commercially available materials. Herein, "comprising"

means that other steps and other ingredients can be in addition. "Comprising" encompasses the terms "consisting of" and "consisting essentially of". The compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments, optionally all embodiments or a large subset of embodiments, of the present invention has/have the subsequently described feature. Where amount ranges are given, these are to be understood as being the total amount of said ingredient in the composition, or where more than one species fall within the scope of the ingredient definition, the total amount of all ingredients fitting that definition, in the composition. For example, if the composition comprises from 1% to 5% fatty alcohol, then a composition comprising 2% stearyl alcohol and 1% cetyl alcohol and no other fatty alcohol, would fall within this scope.

The following acronyms are used herein: ACDMT=acryloyldimethyltaurate; AM=acrylamide; AN=acrylonitrile; tBAM=tert.-butyl acrylamide; IBSA=isobutene sulfonic acid; IBDSA=2-methylidene-1,3-propylenedisulfonic acid.

Unless otherwise stated, "viscosity" herein is measured at 20° C. viscosity in centipoise (cP) or mPa·s using a Brookfield viscometer model LV, RVT DV-II or LVT DV-II with 10-90% torque at 20 rpm.

"Molecular weight" or "M.Wt." "Mw", "Mw" or "MW" and grammatical equivalents mean the weight average molecular weight, unless otherwise stated. Also relevant for the determination of the molecular weight distribution is the number average molecular weight "Mn", "Mₑ" and grammatical equivalents, and the polydispersity "D" or "PD".

The weight average molecular weight can be measured by gel permeation chromatography (GPC), also referred to as size exclusion chromatography (SEC). The molecular weight of polymers and its measurement is described in the textbook "Principles of Polymerization" by Georg Odian, third edition, Wiley-Interscience, New York, in chapter 1-4, page 19 to 24, ISBN 0-471-61020-8. The process to determine the weight average molecular weight is described in detail in chapter 3 of Makromolekulare Chemie: Eine Einführung" by Bernd Tieke, Wiley-VCH, 2. vollständig überarbeitete und erweiterte Auflage (3. Nachdruck 2010) ISBN-13: 978-3-527-31379-2, page 259-261.

Determination of molecular weight and distribution of ACDMT samples by GPC was determines under the following conditions.

Column: PSS Suprema 30,000 Å 10 µm, 300 mm×8 mm
Detector: RID
Oven temperature: 23° C.
Flow: 1 ml/min
Injection volume: 20 µl
Eluent: 0.07 mol/l disodium hydrogen phosphate in water
Calibration method: Conventional poly(styrene sulfonate) sodium salt calibration
Sample preparation: Weigh approx. 10 mg sample in 10 ml 0.07 mol/l disodium hydrogen phosphate in water and shake for 15 min.

"Water-soluble" refers to any material that is sufficiently soluble in water to form a clear solution to the naked eye at a concentration of 0.1% by weight of the material in water at 25° C. The term "water-insoluble" refers to any material that is not "water-soluble".

"Substantially free from" or "substantially free of" means less than 1%, or less than 0.8%, or less than 0.5%, or less than 0.3%, or about 0%, by total weight of the composition or formulation.

"Monomer" means a discrete, non-polymerised chemical moiety capable of undergoing polymerisation in the presence of an initiator or any suitable reaction that creates a macromolecule e.g. such as polycondensation, polyaddition, radical, anionic or cationic polymerization. "Unit" means a monomer that has already been polymerised i.e. is part of a polymer.

"Polymer" means a chemical formed from the polymerisation of two or more monomers. The term "polymer" shall include all materials made by the polymerisation of monomers as well as natural polymers. Polymers made from only one type of monomer are called homopolymers. Herein, a polymer comprises at least two monomers. Polymers made from two or more different types of monomers are called copolymers. The distribution of the different monomers can be random, alternating or block-wise (i.e. block copolymer). The term "polymer" used herein includes any type of polymer including homopolymers and copolymers.

"Fuming sulfuric acid" herein means a solution of sulfur trioxide in sulfuric acid. Fuming sulfuric acid is also known as oleum and is identified by the CAS number 8014-95-7, and can be described by the formula $H_2SO_4 \cdot xSO_3$ where x is the molar free sulfur trioxide content.

The "biobased content" is reported in ASTM D6866-12, Method B (see section 3.3.9 of ASTM D6866-12). "Biobased carbon content", "biobased content", "biogenic carbon content", "bio-based content", "biomass-derived carbon" herein refer to the same thing and are all measured in wt. %. Herein, the term 'bio-based carbon content' is used. ASTM D6866-12, Method B lab results report the percentage of bio-based carbon content relative to total carbon, and not to total mass of the sample or molecular weight. A comment on bio-based carbon content calculation: Presently ASTM D6866-12, Method B (see section 9 of ASTM D6866-12) requires the percent modern carbon value (pMC) reported to be multiplied by a correction factor of 0.95 to account for excess carbon-14 in the atmosphere due to nuclear weapons testing. However, a revision is pending for ASTM D6866-12, Method B to update the correction factor to 0.98 due to ongoing decrease in excess atmospheric $^{14}CO_2$. For the purposes of accuracy, the new correction factor of 0.98 is often reported in the field e.g. by suppliers. Generally, results below ~20% bio-based carbon will not be affected. However, results close to 100% will be ~2-3% bio-based carbon higher using the 0.98 factor vs 0.95. Results between ~20-90% will increase by 0-3%. Hence the term "bio-based carbon content" as used herein is defined by the equation:

$$\text{Bio-based carbon content} = pMC*0.95 (\%)$$

A review on measurement methods of bio-based carbon content for biomass-based chemicals and plastics is given by Massao Kunioka in *Radioisotopes*, 62, 901-925 (2013).

Explanation of and benefits provided by the invention

Surprisingly, it has now been found that it is possible to synthesise good quality bio-based ACDMT at acceptable yields. Indeed, when considering genetically engineered microbes for use in creating bio-based ACDMT, currently no such microbes are commercially available. ACDMT itself is not similar to any other products that typical microbes would produce naturally. Furthermore, there are few natural microbial pathways capable of converting sulfonic acid groups. Therefore, the person skilled in the art naturally has a bias in his mind that it would be difficult to produce bio-based ACDMT in view of its more synthetic-type chemical moieties. The person skilled in the art, may however, consider that the reaction of acrylic acid with taurine, as bio-based materials could form the corresponding acryl-amido taurate compound, which is a similar structure as compared to ACDMT. However, the reactants would preferentiality react to form a Michael adduct, rather than an acryl-amido taurate compound. Hence, it is known to the person skilled in the art that synthesising bio-based ACDMT is no trivial matter.

Bianca et al (Appl Microbiol Biotechnol (2012) 93:1377-1387) states that a high level of impurities are produced when bio-based isobutene is synthesised (⅔ carbon dioxide). WO2014086780A2 on pages 5 and 6 mentions various by-products and impurities that may result from the bio-based isobutene is synthesised. Indeed, on page 14 of WO2014086780A2 it states "The fermentation off-gas (i.e. a gas stream originating from the fermenter) typically comprises the hydrocarbon as the desired product and the intermediate together with additional gaseous components. Generally, the total content of the desired product, such as isobutene, and the intermediate, such as acetone, in the fermentation off-gas is in a range of 3 to 30 vol. %, preferably 3 to 20 vol. %.". In other words, it is known in the art that a very low yield results when known bio-based isobutene synthesis processes are employed, as well as that significant level of by-products is produced. Indeed, normally at least 98%, typically at least 99.5% purity of isobutene is used in conventional synthesis techniques. Surprisingly, it is possible to produce bio-based ACDMT despite using bio-based components that are typically impure in view of the microbes that produce the bio-based component creating by-products as a result of their natural enzymatic action.

The present invention relates inter alia to bio-based acryloyldimethyltaurate (ACDMT) and polymers comprising at least one unit from bio-based ACDMT. The invention is characterized in that at least one portion of the carbons thereof is biologically sourced and, more specifically, in that it contains between 38 wt. % and 100 wt. % bio-based carbon content in relation to total carbon weight according to the ASTM D6866-12, Method B standard. The preparation method typically comprises the use of acrylonitrile, isobutene and a mixture of sulfuric acid and fuming sulfuric acid comprising sulfur trioxide. Preferably, at least one of the raw materials, acrylonitrile or isobutene, are of bio-based origin. The bio-based ACDMT is suitable to make polymers comprising a bio-based carbon content stemming from its bio-based ACDMT share.

ACDMT (see Formula [3]) consists of seven carbon atoms. Preferably a minimum of three, preferably four and most preferred all seven carbon atoms of the ACDMT molecule can become renewable, bio-based carbon atoms. In this way, a high proportion of bio-based and/or biodegradable (polymer) products made from the bio-based monomer ACDMT are recyclable and part of the natural carbon cycle. If these kinds of products are incinerated or biodegraded, the quantity of carbon dioxide that is emitted corresponds to the quantity fixed by photosynthesis during biomass growth.

To date several high performance water soluble or water swellable polymers such as Fluid Loss Additives for the construction and (oil and gas) well construction industry as well as rheology modifiers, comprise ACDMT. Independent from the excellent performance in their applications, such polymers have so-far all been made from petrochemical based, fossil hydrocarbon based ACDMT. The present invention provides new bio-based ACDMT thus giving access to polymers comprising bio-based ACDMT.

The details of the invention and its aspects are provided hereinafter.

First Aspect

The first aspect relates to a compound according to Formula (3), wherein the compound comprises from 28 wt. % to 100 wt. % bio-based carbon content, relative to the total mass of carbon in the compound, measured according to standard ASTM D6866-12, Method B;

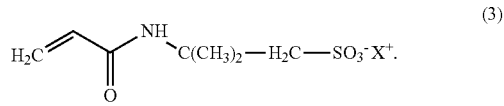

and wherein $X^+$ is a proton.

The compound comprises from 28 wt. % to 100 wt. % bio-based carbon content, relative to the total mass of carbon in the compound, measured according to standard ASTM D6866-12, Method B. In at least one embodiment, the compound comprises from 35 wt. %, preferably from 40 wt. %, more preferably from 54 wt. %, even more preferably from 57 wt. % to 100 wt. %, most preferably about 100 wt. %, by mass of bio-based carbon content, relative to the total mass of carbon in the compound, measured according to standard ASTM D6866-12, Method B.

Preferably the compound according to Formula (3) is ACDMT.

The bio-based carbon content, relative to the total mass of carbon in the compound, is measured according to standard ASTM D6866-12, Method B. More details on the analytical procedure for determination of bio-based carbon content: the provided sample material does not undergo any pre-treatment procedure and is converted to graphite as is using the following procedure:

Depending on the estimated amount of carbon content, typically a few milligrams of sample material is combusted in an elemental analyzer (EA). The resulting gas mixture is cleaned and $CO_2$ is automatically separated by the EA using the purge and trap technology. The remaining $CO_2$ is transferred into a custom-made graphitization system, converted into carbon (graphite) catalytically using $H_2$ and an iron-powder catalyst. The $^{14}C$ determination of the graphite is performed at the Klaus-Tschira-Archaeometrie-Center using an accelerator mass-spectrometer (AMS) of the type MICADAS (developed at the ETH Zurich, Switzerland).

Second Aspect

A second aspect relates to a compound, according to Formula (3), derived from isobutene, wherein the isobutene has at least 90 wt. % bio-based carbon content, relative to the total mass of carbon in isobutene, measured according to standard ASTM D6866-12, Method B;

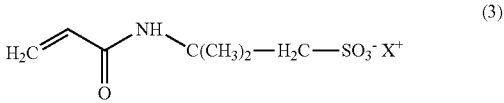

and wherein X⁺ is a proton. Herein "derived from isobutene" means that the compound is obtained by employing isobutene e.g. using isobutene as a reactant in order to synthesise the compound.

The second aspect also relates to a compound, according to Formula (3), derived from acrylonitrile, wherein the acrylonitrile has at least 90 wt. % bio-based carbon content, relative to the total mass of carbon in acrylonitrile, measured according to standard ASTM D6866-12, Method B;

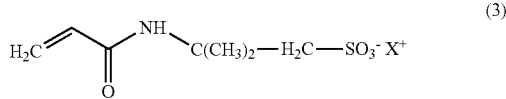

(3)

and wherein X⁺ is a proton. Herein "derived from acrylonitrile" means that the compound is obtained by employing acrylonitrile e.g. using acrylonitrile as a reactant in order to synthesise the compound.

In at least one embodiment, the compound is derived from both isobutene and acrylonitrile, wherein the isobutene has at least 90 wt. % bio-based carbon content, relative to the total mass of carbon in isobutene, measured according to standard ASTM D6866-12, Method B; and wherein the acrylonitrile has at least 90 wt. % bio-based carbon content, relative to the total mass of carbon in acrylonitrile, measured according to standard ASTM D6866-12, Method B;

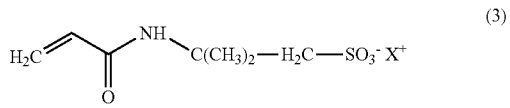

(3)

and wherein X⁺ is a proton. Herein "derived from both isobutene and acrylonitrile" means that the compound is obtained by employing both acrylonitrile and isobutene e.g. using acrylonitrile and isobutene as reactants in order to synthesise the compound.

In at least one embodiment, the isobutene has at least 95 wt. %, preferably about 100 wt. % bio-based carbon content, relative to the total mass of carbon in isobutene, measured according to standard ASTM D6866-12, Method B. In at least one embodiment, the isobutene is obtained from a genetically modified microorganism, preferably from genetically modified *Escherichia coli*. In at least one embodiment, the isobutene is derived from 3-methylcrotonyl-CoA In at least one embodiment, the acrylonitrile has at least 95 wt. %, preferably about 100 wt. % bio-based carbon content, relative to the total mass of carbon in acrylonitrile, measured according to standard ASTM D6866-12, Method B.

In at least one embodiment, the compound, according to Formula (3), is obtained from reacting acrylonitrile, fuming sulfuric acid and isobutene in a suitable solvent, wherein the isobutene has at least 90 wt. % bio-based carbon content, relative to the total mass of carbon in isobutene, measured according to standard ASTM D6866-12, Method B; and/or wherein the acrylonitrile has at least 90 wt. % bio-based carbon content, relative to the total mass of carbon in acrylonitrile, measured according to standard ASTM D6866-12, Method B.

Third Aspect

A third aspect relates to a polymer obtained by polymerising at least one compound according to the first aspect or the second aspect. In at least one embodiment, the compound according to the first aspect or the second aspect is neutralised with a base prior to polymerisation.

In at least one embodiment, the polymer has been neutralized following polymerization using a base. In at least one embodiment, the polymer comprises at least one repeating unit according to Formula (1), wherein $R^1$ and $R^2$ are H; A is $-C(CH_3)_2-H_2C$; and $Q^+$ is a cation;

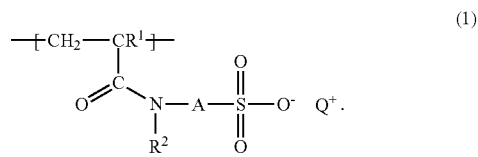

(1)

In at least one embodiment, $Q^+$ is $H^+$, $NH_4^+$, morpholine, an organic ammonium ion $[NHR^5R^6R^7]^+$ wherein $R^5$, $R^6$, and $R^7$ independently of one another is hydrogen, a linear or branched alkyl group having 1 to 22 carbon atoms, a linear or branched, mono- or poly-unsaturated alkenyl group having 2 to 22 carbon atoms, a $C_6$-$C_{22}$ alkylamidopropyl group, a linear mono-hydroxyalkyl group having 2 to 10 carbon atoms or a linear or branched dihydroxyalkyl group having 3 to 15 carbon atoms, and wherein at least one of the radicals $R^5$, $R^6$, and $R^7$ is not hydrogen, or $X^+$ is $Li^+$, $Na^+$, $K^+$, ½ $Ca^{++}$, ½ $Mg^{++}$, ½ $Zn^{++}$, ⅓ $Al^{+++}$, or combinations thereof. Preferably $Q^+$ is $H^+$, $NH_4^+$ or $Na^+$.

Most preferably, $Q^+$ is $Na^+$. In at least one embodiment, $Q^+$ is $NH_4^+$. In at least one embodiment, $Q^+$ is selected from the group monoalkylammonium, dialkylammonium, trialkylammonium and/or tetraalkylammonium salts, in which the alkyl substituents of the amines may independently of one another be ($C_1$ to $C_{22}$)-alkyl radicals or ($C_2$ to $C_{10}$)-hydroxyalkyl radicals.

In at least one embodiment, the repeating units according to Formula (1) have a degree of neutralisation of between 0 mol-% and 100 mol-%. In at least one embodiment, the repeating units according to Formula (1) have a degree of neutralisation of from 50.0 to 100 mol-%, preferably from 80 mol-% to 100 mol-%, more preferably from 90.0 to 100 mol-%, even more preferably from 95.0 to 100 mol-%. Particular preference being given to a degree of neutralisation of more than 80%, more preferably more than 90%, even more preferably more than 95%.

In at least one embodiment, the polymer has a weight average molecular weight of at least 700 g/mol, preferably from 700 g/mol to 10 million g/mol.

In at least one embodiment, the polymer is substantially free of units not being those according to Formula (1), wherein $R^1$ and $R^2$ are H; A is $-C(CH_3)_2-H_2C$; and $Q^+$ is a cation. In at least one embodiment, the polymer is a homopolymer.

In at least one embodiment, the polymer is a copolymer of units according to those according to Formula (1), wherein $R^1$ and $R^2$ are H; A is $-C(CH_3)_2-H_2C$; and $Q^+$ is a cation, and at least one further unit.

In at least one embodiment, the polymer is a rheology modifier or a thickening agent, or is suitable for use therefor.

Fourth Aspect

A fourth aspect relates to a process for synthesising a compound according to Formula (3), comprising reacting acrylonitrile, fuming sulfuric acid and isobutene in a suitable solvent; wherein the isobutene has at least 90 wt. % bio-based carbon content, relative to the total mass of carbon in isobutene, measured according to standard ASTM D6866-12, Method B; and/or wherein the acrylonitrile has at least 90 wt. % bio-based carbon content, relative to the total mass of carbon in acrylonitrile, measured according to standard ASTM D6866-12, Method B;

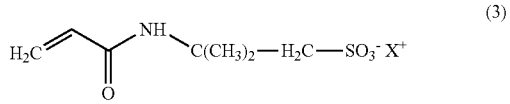

(3)

and wherein $X^+$ is a proton.

The process occurs in a suitable solvent. "In a suitable solvent" may mean that the acrylonitrile itself functions as the solvent. Alternatively, a compound not being acrylonitrile can function as the solvent. In a preferred embodiment, the acrylonitrile itself functions as the solvent. In at least one embodiment, the solvent is selected from aprotic polar solvents. In at least one embodiment, the solvent is selected from the group consisting of: tetrahydropyran, tetrahydrofuran, 2-methyltetrahydrofuran, 1,3-dioxane, 1,4-dioxane, dimethylketone, ethyl-methy-ketone, methyl-tert.-butylketone, tetrahydrofuran, 2-methyltetrahydrofuran, 1,3-dioxaneacetic acid anhydride, ethyl acetate, di-methylformamide and mixtures thereof. Preferably the solvent is selected from the group consisting of: tetrahydrofuran, 2-methyltetrahydrofuran, dimethylketone, ethyl-methyl-ketone, methyl-tert.-butylketone, 2-methyltetrahydrofuran, acetic acid anhydride, ethyl acetate, di-methylformamide and mixtures thereof. More preferably the solvent is selected form the group consisting of: tetrahydrofuran, 2-methyltetrahydrofuran, dimethylketone, ethyl-methy-ketone, methyl-tert.-butylketone, acetic acid anhydride, ethyl acetate and mixtures thereof. Most preferably the solvent is selected from acetic acid anhydride and ethyl acetate, or a mixture thereof.

In at least one embodiment, the level of solvent in wt. % is higher than that of the level of compound according to Formula (3).

In at least one embodiment, the solvent is used at a concentration of 5 to 80 wt.-%, preferably 10 to 70 wt.-%, more preferably from 20 wt.-% to 60 wt.-% by weight of the total mixture. "Total mixture" here means the total reaction mixture and thus including acrylonitrile, fuming sulfuric acid and isobutene.

In at least one embodiment, the process comprises:
(a) a first step of mixing fuming sulfuric acid with the acrylonitrile to produce a mixture of acrylonitrile and fuming sulfuric acid in an aprotic polar solvent;
(b) a second step of contacting the mixture produced in the first step, with the isobutene, to obtain an aprotic polar solvent slurry of compound according to Formula (3)

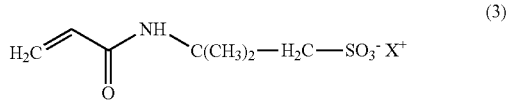

(3)

wherein $X^+$ is a proton;
(c) optionally a third step of subjecting the slurry obtained in the second step, to solid-liquid separation to obtain a cake of crude compound according to Formula (3), and then washing the cake with an aprotic polar solvent of mass of at least two times that of the cake, and (d) optionally a fourth step of drying the cake washed in the third step.

In at least one embodiment, the first step is carried out at a temperature of from −50° C. to 10° C. In at least one embodiment, the second step is carried out at a temperature of from 10° C. to 70° C.

In at least one embodiment, the process subsequently comprises isolating a compound according to Formula (3);

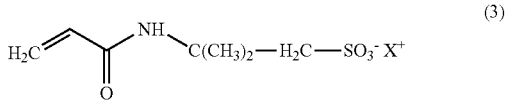

(3)

wherein $X^+$ is a proton; and then optionally employing said compound to synthesise a polymer.

In at least one embodiment, the process is carried out as a batch process or as a continuous process.

The reaction to form bio-based ACDMT can be advantageously controlled to form and to isolate useful by-products of the reaction. Useful by-products include, for example, bio-based acrylamide and/or bio-based tert.-butylacrylamide. Both substances can be isolated and both substances can be useful monomers. In at least one embodiment, the tert.-butylacrylamide comprises from 28 wt. % to 100 wt. % bio-based carbon content, relative to the total mass of carbon in the tert.-butylacrylamide, measured according to standard ASTM D6866-12, Method B. In at least one embodiment where bio-based acrylonitrile with a bio-based content of at least 90 wt. % is used, the produced acrylamide comprises from 90 wt. % to 100 wt. % bio-based carbon content, relative to the total mass of carbon in the acrylamide, measured according to standard ASTM D6866-12, Method B.

Fifth Aspect

A fifth aspect relates to the use of the compound of the first or second aspect as a monomer for synthesizing a polymer.

Sixth Aspect

A sixth aspect relates to the use of the polymer according to the third aspect as a thickening agent and/or rheology modifier. For example, the thickening agent and/or rheology modifier can be used as an additive in the oil and mining industry e.g. to increase the efficiency of processes for isolating crude oil.

Seventh Aspect

A seventh aspect relates to a composition comprising the compound of the first or second aspect. In at least one embodiment, the composition comprises at least 50 wt. % of said compound. In an alternative composition, the composition comprises a polymer according to the third aspect. In at least one embodiment, the composition comprises at least 50 wt. % of the polymer.

Eighth Aspect

An eighth aspect relates to a method of polymerizing a polymer according to the third aspect. In at least one embodiment, the method employs solution polymerization. In at least one embodiment, the method employs precipitation polymerization. In at least one embodiment, the precipitation polymerization is in a tert.-butanol solvent.

EXAMPLES

The examples which follow are intended to illustrate the subject matter of the invention, without restricting it thereto.

Isobutene samples used:

The composition of petroleum-based isobutene is different from bio-based isobutene. Bio-based isobutene contains exclusively contemporary carbon and hence has a different distribution of carbon isotopes as compared to fossil, petrochemical-based carbon. Fossil carbon was cut off from the natural carbon equilibrium for millions of years and all the natural $^{14}C$ has already degraded, and hence the concentration of $^{14}C$ is zero in fossil carbon sources. Contemporary carbon, produced by living organisms is part of the atmospheric carbon isotope equilibrium. $^{14}C$ or radiocarbon is constantly being created in the atmosphere by the interaction of cosmic rays with atmospheric nitrogen. The resulting radiocarbon combines with atmospheric oxygen to form radioactive carbon dioxide, which is incorporated into plants by photosynthesis; animals then acquire $^{14}C$ by eating the plants. When the animal or plant dies, it stops exchanging carbon with its environment, and from that point onwards the amount of $^{14}C$ it contains begins to decrease as the $^{14}C$ undergoes radioactive decay. Therefore, in contemporary carbon the concentration of $^{14}C$ is in the order of $10^{-10}$%. Masao Kunioka recently described "Measurement Methods of Biobased Carbon Content for Biomass-based Chemicals and Plastics" in *Radioisotopes*, 62,901-925 (2013).

Interestingly enough also the chemical composition of bio-based and petrochemical-based isobutene is different in several aspects. Table 1 shows differences in the composition for the isobutene samples used in the present invention. Petrochemical-based isobutene contains small amounts of petrochemical by-products such as propane, propene, butane and isobutane, but it does not contain any traces of metabolic products (Type Petro, IB1). In contrast to the petrochemical isobutene, the bio-based samples contain carbon dioxide and small quantities of ethanol as metabolic products from the microorganisms (Type Bio, samples IB2 to IB5). The bio-based isobutene samples do not contain any propane, propene, butane or isobutane.

TABLE 1

| Isobutene | | Isobutene sample qualities used | | | | | | | |
|---|---|---|---|---|---|---|---|---|---|
| | | Isobutene | $N_2$ | $CO_2$ | $H_2O$ | ethanol | propane | Propene | Iso-butane | n-butane |
| sample | type | m/v % | m/v % | m/v % | m/v % | m/v % | m/v % | m/v % | m/v % | m/v % |
| IB1 | Petro | 99.873 | ND | ND | 0.06 | ND | 0.0003 | 0.0018 | 0.0639 | 0.001 |
| IB2 | Bio | 99.72 | 0.1 | 0.3 | 0.03 | 0.002 | ND | ND | ND | ND |
| IB3 | Bio | 92.07 | 3.2 | 4.7 | 0.03 | 0.005 | ND | ND | ND | ND |
| IB4 | Bio | 21.94 | 60 | 18 | 0.05 | 0.008 | ND | ND | ND | ND |
| IB5 | Bio | 97.7 | 2 | 0.26 | 0.03 | 0.002 | ND | ND | ND | ND |

KEY: ND = not detected.

Compared with the quality of petrochemically acquired isobutene, the amount of impurities in the bio-based isobutene are significantly higher and the composition is different. Especially IB4 contains only 21.94% isobutene and 18% carbon dioxide. Surprisingly it was found that it was possible to synthesize ACDMT with high purity based on the isobutene with high levels of impurities.

TABLE 2

| Acrylonitrile sample qualities used | | | | | |
|---|---|---|---|---|---|
| Acrylonitrile sample | Type | Acrylonitrile | $H_2O$ as is | $H_2O$ after drying | 4-methoxy-phenol |
| | | Units | | | Ppm |
| AN1 | Petro | 99.2 | 0.41 | 19 | 43 |
| AN2 | Bio | 99.1 | 0.53 | 21 | 56 |

Acrylonitrile ≥99%, from Sigma-Aldrich contains 35-45 ppm monomethyl ether hydroquinone as inhibitor, contained 0.41% water before drying. It was dried by adding 50 g molecular sieve 0.4 nm from Merck Millipore, Merck KGaA. The residual water content of the acrylonitrile was 19 ppm, measured by Karl-Fischer titration (DIN 51777). The biologically acquired acrylonitrile was relatively similar in chemical composition as compared to the petrochemical one. The used acrylonitrile was obtained in two steps via oxidative decarboxylation of glutamic acid and subsequent decarbonylation elimination of 3-cyanopropionic acid to form acrylonitrile using the method described in *Green Chemistry*, 2011, 13, 807.

Comparative example 1 (CompEx1), using conventional petrochemical raw materials in a batch process:

The reactor was a 5 neck 250 ml round bottom flask, equipped with an overhead agitator, thermocouple, sub surface gas injection pipe, intensive condenser and dropping funnel with pressure compensation. The head of the condenser was equipped with a dry tube containing 50 g of 4 Angstrom molecular sieve. A PTFE plate stirrer with precision glass joint seal was connected to the overhead stirrer. 150 ml dry acrylonitrile was dosed to the reactor. Under stirring at 150 rpm the acrylonitrile was cooled with a bath consisting of a mixture of 300 g ice and 100 g NaCl. As soon as the reactor temperature reaches −10° C. 39.30 g 100% sulfuric acid was slowly dosed. The temperature was kept in a range of −10 to −7.5° C. The time for dosing the sulfuric acid was 40 minutes. The liquid stayed clear. Then the ice bath was removed and replaced by a water bath at 21° C. 9.9 L of isobutene was dosed at a rate of 10 L/h. The temperature was allowed to climb quickly, but controlled to be stable at 40° C. for the course of the dosage. After approximately 35 min., fine white crystals started to precipitate. After dosage was completed the reaction mixture was stirred for one hour at 40° C. Then the reaction mixture was cooled under agitation for 30 min. to 20° C. The reaction mixture was a fine white suspension. The solid was separated by vacuum filtration over glass fiber filter, stirred with 50 g fresh acrylonitrile in a 250 ml Erlenmeyer-flask for 10 minutes using a magnetic stirrer, PTFE coated stirrer bar and covered with a glass lid. The solids of the suspension was removed again by vacuum filtration over a glass fiber filter (Whatman Grade GF/D). The solid was dried for 4 hours in a laboratory rotation evaporator at a bath temperature of 60° C., starting at a pressure of 300 mbar. After 30 minutes the pressure was ramped down to 10 mbar in 3 h.

With a yield of 85 wt. % ACDMT was isolated with a purity of 95.9 wt. %. 0.3 wt. % acrylonitrile, 0.6 wt. % acrylamide, 2.9% tert. butylacrylamide and 0.3 wt. % 2-methylprop-2-en-1-sulfonic acid were found.

The comparative Examples CompEx2 to CompEx3 were carried out in the same way, but the sulfur trioxide excess was increased. Please see Table 3.

Comparative example 4 (CompEx4) (see US2010/0274048) for a continuous process with conventional petrochemical raw materials:

Two glass reactors each provided with a stirrer, an inlet pipe and an outlet pipe were connected to each other. Acrylonitrile and sulfuric acid were fed by peristaltic pumps into the first reactor. With a flow rate of 47.1 g/h sulfuric acid and 22.36 g/h 20% commercial fuming sulfuric acid and 161.1 g/h dry acrylonitrile was pumped. The sulfuric acid was 97% concentrated. The concentration of sulfur trioxide in fuming sulfuric acid was chosen to compensate for the water carried by the raw materials acrylonitrile and isobutene. The temperature of the reaction mixture in the first reactor was kept at −10±2.5° C. The average residence time was 90 minutes. Sulfonic acid and acrylonitrile were mixed and the mixed fluid thereof was fed into the second reactor. The second reactor was a three neck 250 ml round bottom reactor, modified with a side neck to allow overflow of the reactor to a beaker. It was connected with an overhead stirrer, glass stirrer with PTFE stirrer blades and an intensive condenser. In the second reactor, isobutylene gas (IB1) was blown sub surface with a flow rate of 30.8 g/h into the mixed fluid to synthesize ACDMT. The reaction (synthesis) was conducted continuously with an average residence time of 90 minutes at a temperature of 40±2.5° C. After 11 h continuously conducted reaction a sample of the reaction mixture was taken and analyzed.

The ACDMT slurry obtained in the above production was suction-filtered using a glass filter to obtain a cake on the glass filter. Acrylonitrile of an amount (mass) shown in Table 5, relative to the mass of the cake was poured onto the cake. Suction filtering was conducted again to wash the cake with acrylonitrile.

The washed cake was dried for 360 minutes at a temperature of 80° C. with a rotational evaporator at reduced pressure. A vacuum of 400 mbar was applied for 30 minutes. Then the pressure was ramped down to 10 mbar in 2 hours and maintained at 10 mbar until drying was completed.

The yield determined was related to the sample size drawn. The ACDMT powder obtained was analyzed by HPLC to measure the concentrations of acrylonitrile (abbreviated as AN), acrylamide (abbreviated as AM), tert.-butylacrylamide (abbreviated as tBAM), 2-methyl-2-propenyl-1-sulfonic acid (abbreviated as IBSA). The results of the comparative experiment is shown in table 6.

EXAMPLE 1

The reactor was a 5 neck 250 ml round bottom flask, equipped with an overhead agitator, thermocouple, sub-surface gas injection pipe, intensive condenser and dropping funnel with pressure compensation. The head of the condenser was equipped with a dry tube containing 50 g of 4 Angstrom molecular sieve. A PTFE plate stirrer with precision glass joint seal was connected to the overhead stirrer. 150 ml dry acrylonitrile was dosed to the reactor. Under stirring at 150 rpm the acrylonitrile was cooled with a bath consisting of a mixture of 300 g ice and 100 g NaCl. Alternatively the mixture could be cooled down with a combination of acetone and dry ice. As soon as the reactor temperature reaches −10° C., 49.30 g 100% sulfuric acid was slowly dosed. The access of sulfur trioxide was controlled to compensate for the water content of the raw materials isobutene and acrylonitrile. The variation of the process conditions were documented in table 3. The temperature was kept in a range of −10 to −7.5° C. The time for dosing the sulfuric acid was 40 minutes. The liquid stays clear.

Then the ice bath was removed and replaced by a water bath at 21° C. 9.9 L of bio-based isobutene was dosed at a rate of 10 L/h. The temperature was kept allowed to climb quickly, but controlled to stay at 40° C. for the course of the dosage. After approximately 25 min., fine white crystals started to precipitate. After dosage was completed the reaction mixture was stirred for one hour at 40° C. Then the reaction mixture was cooled under agitation for 30 min. to 20° C. The reaction mixture was a fine white suspension. The solid was separated by vacuum filtration over glass fiber filter, stirred with 50 g fresh acrylonitrile in a 250 ml Erlenmeyer-flask for 10 minutes using a magnetic stirrer, PTFE coated stirrer bar and covered with a glass lid. The solids of the suspension was removed again by vacuum filtration over a glass fiber filter (Whatman Grade GF/D). The solid was dried for 4 hours in a laboratory rotation evaporator at a bath temperature of 80° C., starting at a pressure of 300 mbar, after 30 minutes the pressure was ramped down to 10 mbar in 3 h.

TABLE 3

Reaction conditions for batch reactions

| Experiment | AN [g] | Material | $H_2SO_4$, 100% [g] | Oleum 20% $SO_3$ [g] | Isobutene [g] | material | Flow rate [L/h] | T1 [° C.] | T2 [° C.] |
|---|---|---|---|---|---|---|---|---|---|
| CompEx1 | 150 | AN1 | 49.3 | 0.0 | 28.1 | IB1 | 10 | −10 | 40 |
| CompEx2 | 150 | AN1 | 49.1 | 0.10 | 28.1 | IB1 | 10 | −10 | 40 |
| CompEx3 | 150 | AN1 | 48.9 | 0.2 | 28.1 | IB1 | 10 | −10 | 40 |
| 1 | 150 | AN1 | 49.2 | 0.08 | 28.1 | IB2 | 10 | −10 | 40 |
| 2 | 150 | AN1 | 49.2 | 0.09 | 30.5 | IB3 | 11 | −10 | 40 |
| 3 | 150 | AN1 | 48.6 | 0.56 | 128 | IB4 | 23 | −10 | 40 |

TABLE 3-continued

| | | | Reaction conditions for batch reactions | | | | | |
|---|---|---|---|---|---|---|---|---|
| | AN | Material | $H_2SO_4$, 100% | Oleum 20% $SO_3$ | Isobutene | material | Flow rate | T1 | T2 |
| Experiment | [g] | | [g] | [g] | Unit [g] | | [L/h] | [° C.] | [° C.] |
| 4 | 150 | AN1 | 49.2 | 0.08 | 28.8 | IB5 | 10 | −10 | 40 |
| 5 | 50 | AN2 | 16.4 | 0.03 | 9.6 | IB5 | 10 | −10 | 40 |

The results of the comparative experiments and the experiments describing the invention are summarized in table 4.

The experiments demonstrate that the precipitation of ACDMT starts earlier with the bio-based isobutene as compared to the petro-chemical produced isobutene. Also it was found that the use of bio-based isobutene was suitable make bio-based ACDMT. Surprisingly, the purity of the bio-based ACDMT is higher as compared to the comparative experiments 1 to 3. In particular the impurities t-BAM and IBSA were reduced. The potential side products IBSA and IBDSA act to moderate (control) the molecular weight in the radical polymerization. Hence a person skilled in the art would expect the molecular weight of a polymer in the presence of a larger amount of a moderator to be lower as compared to one polymerized under the same conditions with a lesser amount of moderator. As an IBDSA standard was not available the amount of IBDSA was not quantified.

A surprising advantage of the invention is that bio-based isobutene can be used in the ACDMT production process with a lower quality as compared to petrochemically-manufactured isobutene to produce an as good or better quality of ACDMT.

To test the bio-based content, three samples were investigated according to ASTM D6866-12, Method B. CompEx1 was made with conventional, petrochemical raw materials. Therefore it is to be expected that all carbon is fossil carbon. Consequently no $^{14}C$ should be found and the bio-based carbon content should be zero. In this experiment, the investigation indeed returned a bio-based carbon content of 0 wt. %. In Experiment 1, a sample of bio-based isobutene (IB2) was used. As four of the seven ACDMT carbon atoms were replaced by bio-based carbon, in theory 57 wt. % bio-based carbon should be found. The experiment delivers a bio-based carbon content of 55 wt. %. The deviation of the theoretical value can be explained by the impurity of the material and the analytical error of 2% of the method.

EXAMPLE 6

Two glass reactors each provided with a stirrer, an inlet pipe and an outlet pipe were connected to each other. Acrylonitrile and sulfuric acid were fed by peristaltic pumps into the first reactor. With a flow rate of 47.1 g/h sulfuric acid and 22.36 g/h 20% commercial fuming sulfuric acid and 161.1 g/h dry acrylonitrile was pumped. The sulfuric acid was a 97% concentrate. The concentration of sulfur trioxide in fuming sulfuric acid was chosen to compensate for the water carried by the raw materials acrylonitrile and isobutene. The temperature of the reaction mixture in the first reactor was kept at −10±2.5° C. The average residence time was 90 minutes. Sulfonic acid and acrylonitrile were mixed and the mixed fluid thereof was fed into the second reactor. The second reactor was a modified there neck 250 ml round bottom reactor, connected with an overhead stirrer, glass stirrer with PTFE stirrer blades and an intensive condenser. In the second reactor, isobutylene gas (IB2) was blown sub surface with a flow rate of 30.8 g/h into the mixed fluid to synthesize ACDMT. The reaction (synthesis) was conducted continuously with an average residence time of 90 minutes at a temperature of 40±2.5° C. After 11 h continuously conducted reaction a sample of the reaction mixture was taken and analyzed.

The ACDMT slurry obtained in the above production was suction-filtered using a glass filter to obtain a cake on the glass filter. Acrylonitrile of an amount (mass) shown in Table 5, relative to the mass of the cake, was poured onto the cake. Suction filtering was conducted again to wash the cake with acrylonitrile. The solid was dried for 2 hours in a laboratory rotation evaporator at a bath temperature of 80° C., starting at a pressure of 400 mbar, after 30 minutes the pressure was ramped down to 10 mbar in 1 h.

The reaction was run for 12 h evaluated was the sample drawn at 11 h run time.

TABLE 4

| | | | | | | | | Bio-based |
|---|---|---|---|---|---|---|---|---|
| | Yield | | ACDMT | AM | AN | t-BAM | IBSA | content |
| Experiment | [g] | [%] | [wt.-%] | [wt.-%] | [wt.-%] | [wt.-%] | [wt.-%] | [wt.-%] |
| CompEx1 | 91.1 | 88 | 95.9 | 0.6 | 0.3 | 2.9 | 0.3 | 0 |
| CompEx2 | 93.5 | 90 | 97.1 | 0.3 | 0.3 | 2.1 | 0.2 | ND |
| CompEx3 | 91.6 | 88.5 | 96.2 | 0.3 | 0.3 | 1.9 | 0.4 | ND |
| 1 | 98.4 | 95 | 99.4 | 0.07 | 0.06 | 0.45 | 0.05 | 55 |
| 2 | 98.2 | 95 | 98.9 | 0.08 | 0.09 | 0.51 | 0.03 | ND |
| 3 | 97.3 | 94 | 98.2 | 0.1 | 0.09 | 0.49 | 0.06 | 56 |
| 4 | 98.3 | 95 | 99.5 | 0.05 | 0.04 | 0.39 | 0.02 | ND |
| 5 | 33.0 | 95.5 | 99.2 | 0.04 | 0.04 | 0.41 | 0.03 | 99 |

KEY: ND = not detected; ACDMT = acryloyldimethyltaurate; AM = acrylamide; AN = acrylonitrile; tBAM = tert.-butyl acrylamide; IBSA = isobutene sulfonic acid.

The yield determined was related to the sample size drawn.

The ACDMT powder obtained was analyzed by HPLC to measure the concentrations of acrylonitrile.

The results of the comparative experiment was shown in table 6.

Examples 7 to 10 were run according to the same method. The parameters are summarized in table 5.

molecular weight polymers as compared to ACDMT samples with higher IBSA content.

Polymerization process A: solution homopolymer of ACDMT in water.

In a 1-L 5-neck round bottom flask, equipped with an overhead stirrer and an anchor type stirrer, a pH probe, sub-surface nitrogen inlet, dropping funnel, intensive condenser and a gas out let valve 450 g distilled water was filled.

TABLE 5

Reaction conditions for the continuous process

| Experiment | AN [g/h] | material | $H_2SO_4$, 100% [g/h] | Oleum 20% $SO_3$ [g/h] | RT1 [min] | T1 [° C.] | Iso-butene [g/h] | material | RT2 [min] | T2 [° C.] | AN for washing Times filter cake |
|---|---|---|---|---|---|---|---|---|---|---|---|
| CompEx4 | 161.3 | AN1 | 47.8 | 22.36 | 90 | −10 | 30.8 | IB1 | 90 | 40 | 1 |
| 6 | 161.3 | AN1 | 47.8 | 22.28 | 90 | −10 | 30.8 | IB3 | 90 | 40 | 1 |
| 7 | 161.3 | AN1 | 47.8 | 25.10 | 90 | −10 | 139.9 | IB4 | 90 | 40 | 1 |
| 8 | 161.3 | AN1 | 47.8 | 22.28 | 90 | −15 | 30.8 | IB3 | 90 | 40 | 1 |
| 9 | 161.3 | AN1 | 47.8 | 22.28 | 90 | −15 | 30.8 | IB3 | 90 | 45 | 1 |
| 10 | 161.3 | AN1 | 47.8 | 22.28 | 90 | −15 | 30.8 | IB3 | 120 | 45 | 1 |
| 11 | 161.3 | AN1 | 47.8 | 22.28 | 90 | −15 | 30.8 | IB3 | 120 | 45 | 2 |
| 12 | 80.6 | AN2 | 23.9 | 11.14 | 90 | −15 | 30.8 | IB3 | 120 | 45 | 2 |

The continuous process delivers over all cleaner ACDMT as compared to the batch process. The evaluated sample was drawn after running the process steadily for 11 h, because the continuous process with its combined average residence times of 180 and 230 minutes, for example 10 and 11, needs about 9 h to reach a steady state. Table 6 summarizes the results. The comparative experiment 4, experiments 6, 7, 11 and 12 were investigated for their bio-based carbon content. The results are as to be expected considering the choice of raw materials, the purity of the raw material sand the accuracy of the used method according to ASTM 6866-12 Method B. In comparative example 4, petrochemically acquired raw materials were used. In experiments 6, 7 and 11 the bio-based isobutene qualities IB3 and IB4 were used. Hence the 14C method results in 56 and 57 wt. % bio-based carbon. The 57 wt. % bio-based carbon were achieved for the purest ACDMT synthesized. In Experiment 12 both bio-based raw materials, AN2 and IB3 were used. Hence, all carbon in the sample was bio-based, reflected in the finding of 99 wt.-% bio-based carbon.

50 g ACDMT (the ACDMT generated in Example 1) was dissolved. The agitator was set to rotate with 200 rpm. Cooling with a water bath at 20° C. the solution was neutralized with approximately 19 g 50% sodium hydroxide solution to a pH value of 7±0.5. After the neutralization the reaction mixture was heated to 50° C.±0.5° C. temperature. During the heating phase nitrogen was purged through the solution with a flow rate of 60 l/h. The temperature was stabilized and the nitrogen purge continued for 60 minutes. After this 60 minutes the nitrogen was dosed above the liquid surface and the polymerization was initiated by addition of 0.10 g 2,2'-azobis(2-methylpropionamidine)dihydrochloride (V-50 by Wako Specialty Chemicals).

10 minutes after the reaction was started the purge was reduced to 6 l/h. After the temperature maximum was reached the bath temperature was maintained at 50° C. for one hour. Then the bath temperature was increased to 80° C. for 2 h, then cooled to room temperature. The Brookfield viscosity of the solution as was measured at 25° C., 20 rpm, using a spindle delivering a value of 20 to 80% of the maximum scale.

TABLE 6

Results from the continuous process

| Experiment | Yield [wt.-%] | ACDMT | AM [wt.-%] | AN [wt.-%] | t-BAM [wt.-%] | IBSA [wt.-%] | Bio-based carbon [wt.-%] |
|---|---|---|---|---|---|---|---|
| CompEx4 | 88 | 96.1 | 0.311 | 0.267 | 0.135 | 0.184 | 0 |
| 6 | 93 | 99.5 | 0.097 | 0.085 | 0.103 | 0.124 | 56 |
| 7 | 92 | 99.4 | 0.075 | 0.071 | 0.090 | 0.094 | 56 |
| 8 | 94 | 99.5 | 0.051 | 0.048 | 0.081 | 0.098 | ND |
| 9 | 95 | 99.6 | 0.047 | 0.044 | 0.079 | 0.053 | ND |
| 10 | 95 | 99.5 | 0.035 | 0.027 | 0.063 | 0.022 | ND |
| 11 | 96 | 99.7 | 0.033 | 0.027 | 0.062 | 0.018 | 57 |
| 12 | 95 | 99.7 | 0.035 | 0.035 | 0.065 | 0.015 | 99 |

The results acquired from the continuous process show, that the use of bio-based isobutene achieve high yields and high purities. Obviously the use of bio-isobutene leads to a purer ACDMT as compared to petro chemical ACDMT ACDT. Polymerization experiments show especially that ACDMT samples with lower content of IBSA lead to higher Also the Fickenscher k-Value was determined.

Polymerization process B: Homopolymer of ACDMT by precipitation polymerization in tert.-butanol In a 1-Liter Quickfit round bottom flask equipped with a refux condenser, sub surface gas inlet tubing, inner temperature sensor and overhead agitator 400 g tert.-butanol was dosed. 100 g ACDMT according to the invention was charged. The ACDMT was neutralized to a pH of 7 to 8 by injection of gaseous ammonia above the surface. The temperature was kept below 40° C. At agitation of 200 rpm nitrogen was inject subsurface for 1 h. During this time the temperature of the reaction mixture was raised and stabilized to 60° C. with help of a water bath. At 60° C. the pH was readjusted to a pH of 7 to 8. Then the reaction was initiated by the dosage of 1.0 g of 2,2'-azobis(isobutyronitrile).

After a few minutes the polymerization start became obvious by a raising temperature and the precipitation of a polymer. After the temperature maximum was reached the reaction mixture was heated to a gentle reflux for two hours. Then the polymer was cooled to room temperature and dried at 60° C. under a vacuum of 150 mbar.

The resulting polymer powder was dissolved 0.5% in water and the Fickenscher k-value was measured.

Polymerization process C: co-polymer of ACDMT and acrylamide by precipitation polymerisation in tert.-butanol In a 1-Liter Quickfit round bottom flask equipped with a refux condenser, sub surface gas inlet tubing, inner temperature sensor and overhead agitator 400 g tert.-Butanol was dosed. 70 g ACDMT was charged. The ACDMT was neutralized to a pH of 7 to 8 by injection of gaseous ammonia above the surface. The temperature was kept below 40° C. then 30 g of acrylamide was dissolved in the reaction mixture. At agitation of 200 rpm nitrogen was inject subsurface for 1 h. during this time the temperature of the reaction mixture was raised and stabilized to 60° C. with help of a water bath. At 60° C. the pH was readjusted to a pH of 7 to 8. Then the reaction was initiated by the dosage of 1.0 g of 2,2'-azobis(isobutyronitrile).

After a few minutes the polymerization start becomes obvious by a raising temperature and the precipitation of a polymer. After the temperature maximum was reached the reaction mixture was heated to a gentle reflux for two hours. Then the polymer was cooled to room temperature and dried at 60° C. under a vacuum of 150 mbar.

The resulting polymer powder was dissolved 0.5% in water and the Fickenscher k-value was measured.

Analytical Methods Used

Carbon dioxide was determined by gas chromatography:

An Agilent GC 7890 gas chromatograph was equipped with a 1 ml gas loop and coupled to heat transfer detector and a flame ionization detector. The separation column was 30 m long and had a diameter of 0.32 mm with a stationary phase GAS Pro GSC. A first temperature was constant for 5 minutes and then heated with a heat rate of 10° C./min to 240° C. The 240° C. were kept constant for 2 minutes. The Injector temperature was 130° C. and the detector temperature 200° C. The carrier gas helium had a pre pressure of 50 kPa and was flown a 1.2 ml/min. The system was calibrated by 0.2 ml of a propane/butane blend in 1 L air. The amount of $CO_2$ in the air was 300 ppm and 20 ppm propane/butane blend.

The area percent distribution of the sample was detected with an Agilent 6890 GC equipped with a mass sensitive detector type Agilent 5972. The separation column was an Agilent GS-Gaspro 30 m×320 µm (113-4332). A Split/Splitless injection port at 130° C. was used. The manual injection was performed with a gas tight syringe. The Split Mode was 1:10 Split Flow 12.5 ml/min pre pressure 6 kPa. Column parameters: Carrier gas was helium with a constant flow of 1.2 ml/min. Temperature program: 60° C. for 5 min, the with a temperature ramp of 10° C./min the column was heated to 240° C. and kept constant at 240° C. for 10 min. The mass sensitive detector was run in scan-mode of Mz18-270.

Alcohols in isobutene were determined by Gas Chromatography:

The used equipment was an Agilent 7890 A with Deans switching.

The separation column was a 30 m Stabilwax column by Restek with 0.32 mm inner diameter and 0.25 µm film thickness.

The temperature program was 50° C. for 3 min. steady, then ramp 10° C./min to 220° C., 2 min steady at 220° C.

The injector temperature was at 130° C., The temperature at the flame ionization detector (FID) was 240° C.

The combustion gas was hydrogen at 20 ml/min, 350 ml/min synthetic air and makeup-Gas was nitrogen in constant flow of 10 ml/min (column+makeup)

TABLE 7

Polymers

| Example | Polymerization method | Remarks | ACDMT from experiment | Dry matter [wt. %] | Brookfield viscosity 1% [mPas] | Brookfield Viscosity as is [mPa · s] | Fickenscher k-value | GPC Mn [kDa] | GCP Mw [kDa] | GPC D |
|---|---|---|---|---|---|---|---|---|---|---|
| 13 | A | | 1 | 12.62 | ND | | 185 | 510 | 1326 | 2.6 |
| 14 | A | | 3 | 11.23 | ND | | 181 | 480 | 1152 | 2.4 |
| 15 | A | ½ size | 5 | 11.14 | ND | 1210 | 192 | 540 | 1242 | 2.3 |
| CompEx6 | A | | CompEx2 | 11.27 | ND | 810 | 173 | 370 | 851 | 2.3 |
| CompEx7 | A | | CompEx1 | 11.65 | ND | 480 | 132 | 124 | 297.6 | 2.4 |
| | B | | Compex4 | 94.2 | ND | ND | 164 | 340 | 612 | 1.8 |
| | B | | 6 | 95.3 | ND | ND | 187 | 510 | 969 | 1.9 |
| | B | | 7 | 95.8 | ND | ND | 203 | 590 | 1003 | 1.7 |
| | C | | 8 | 94.2 | 21 | ND | 224 | ND | ND | ND |
| | C | | 9 | 94.7 | 23 | ND | 230 | ND | ND | ND |

Drying Acrylonitrile 500 ml acrylonitrile ≥99%, contained 35-45 ppm monomethyl ether hydroquinone as inhibitor from Sigma-Aldrich, contained 0.41% water before drying. It was dried by adding 50 g molecular sieve 0.4 nm from Merck Millipore, Merck KGaA. The residual water content of the acrylonitrile was 19 ppm, measured by Karl-Fischer titration (DIN 51777).

The injector was run in split mode in a 1:20 split. Across the Deans switching a pre pressure of 0.64 bar and a flow rate of 1.15 ml/min helium was used. The results were quantified by the use of an external standard.

The water content was measures by flowing a defined volume of isobutene through a Draeger-tube (Dräger Röhrchen Wasserdampf 0,1, order number (German: Bestellnummer): CH 23 401) and calculate the concentration of water steam in μg/L isobutene gas. A gas flow of 2 L/h was flown through the Draeger tube for 2 minutes. The reading was multiplied by 30 to calculate the result for 1 L isobutene. According to the manufacturer the standard deviation of this method was in the order of 10 to 15% (see Dräger-Röhrchen & CMS-Handbuch, 17. Auflage, März 2015)

The reaction products were determined by high performance liquid chromatography and identification of unknown components in samples were determined using LC/MS-coupling Instrument:
HPLC coupled with mass selective detector; Agilent Technologies; Series 1100; MSD G1956 B
HPLC parameter:
Column: Aquasil C18 150×4.6 mm; 5 μm (Thermo Scientific)
DAD-Detector: Wavelength: UV: 210 nm; (Bw.: 16); Reference: off
Oven temperature: 40° C.
Flow rate: 1.3-1.5 mL/min
Injection volume: 2 μL
Eluents: A: Water+0.1% formic acid (v/v)
B: Acetonitrile
Elution: Gradient:

| Time [min] | % A | % B | Flow [mL/min] |
|---|---|---|---|
| 0 | 98 | 2 | 1.3 |
| 15 | 98 | 2 | 1.3 |
| 20 | 85 | 15 | 1.3 |
| 22 | 85 | 15 | 1.3 |
| 23 | 85 | 15 | 1.5 |
| 27 | 85 | 15 | 1.5 |
| 27.5 | 98 | 2 | 1.3 |

Post time: 7 minutes
MSD parameter:
Ionization source: API-ES
Polarity: Positive and negative
Mode: Scan
Fragmentor: 80 V
Gas temperature: 350° C.
Nebulizer pressure: 45 psig
Drying gas flow: 11 L/min
Capillary voltage: 4000 V
Gain: 1 EMV
Determination of 2-acrylamido-2-methyl-1-propane sulfonic acid, acrylamide, acrylonitrile and 2-methylprop-2-ene-1-sulfonic acid:
Column: Aquasil C18, 5 μm, 250 mm×4.6 mm
Detector: UV at 200 nm
Oven temperature: 40° C.
Flow: 1.5 ml/min/2 ml/min
Injection volume: 5 μl
Eluent: A: water/acetonitrile 98/2 (v/v)+0,005 moll potassium hydrogen sulfate, adjust to pH 3.0 with potassium hydroxide solution (3 mol/L).
B: acetonitrile
Elution: Gradient:

| Time [min] | % A | % B | |
|---|---|---|---|
| 0 | 100 | 0 | 1.5 ml/min |
| 9.99 | 100 | 0 | 1.5 ml/min |
| 10 | 100 | 0 | 2.0 ml/min |
| 15 | 30 | 70 | 2.0 ml/min |
| 15.1 | 30 | 70 | 1.5 ml/min |
| 15.3 | 100 | 0 | 1.5 ml/min |
| 22.0 | 100 | 0 | 1.5 ml/min |

Conditioning time:
Quantification: External standard
Reagents: Solvents: Buffer pH 9.0: Dissolve 4.77 g Sodium tetraborat decahydrat in 1 litre deionized water and add 4.6 ml hydrochloric acid; c(HCl)=1 mol/l
Sample Solvent: Buffer pH 9/water/acetonitrile 37.5/50/12.5 (v/v/v)
Sample preparation:
1. Weight approx. 350 mg sample in 50 g sample solvent
2. dilute sample solutions 1/10 (solid samples), 1/25/liquid samples)
3. then dilute 1/100.
Determination of N-tert-Butylacrylamide:
Column: Aquasil C18; 5 μm, 250 mm×4.6 mm
Detector: UV at 235 nm
Oven temperature: 23° C.
Flow: 1:5 ml/min
Injection volume: 5 μl
Eluent: A: water/acetonitrile 98/2 (v/v)+0.005 molL potassium hydrogen sulfate, adjust pH to 3.0 with potassium hydroxide solution (3 mol/L).
B: acetonitrile
Elution: Gradient:

| Time [min] | % A | % B |
|---|---|---|
| 0 | 70 | 30 |
| 7 | 70 | 30 |

Conditioning time:
Quantification: External standard
Reagents:
Solvents: Buffer pH 9.0: Dissolve 4.77 g Sodium tetraborate decahydrate in 1 litre deionized water and add 4:6 ml hydrochloric acid; c(HCl)=1 mol/l
Sample Solvent: Buffer pH 9/water/acetonitrile 37.5/50/12.5 (v/v/v)
Sample preparation: Weight approx. 350 mg sample in 50 g sample solvent
Determination of the Fickenscher k-value:
This method was used to determine the k-value of certain polymers according to DIN EN ISO 1628-1.

A k-value measurement was a way to indirectly analyze the molecular weight/size of a polymer. A comparatively higher K-value corresponds to a larger molecular weight/size as compared to a polymer with the same composition and made by the same process.

By measuring the measuring the pass-through time of a solvent ($t^0$) and the pass-through time of a polymer solution ($t^c$) through the capillary of an Ubbelhode viscometer the relative viscosity was determined.

$$Z = \frac{t_c}{t_0} = \frac{\eta_c}{\eta_0}$$

From the relative viscosity z the k-value can be calculated according to $$\lg z = \left[\frac{75k^2}{1+150k \times c} + k\right] \times 1$$

In this case $$k = \frac{1.51 \lg z - 1 \pm \sqrt{1 + \left(\frac{2}{c} + 2 + 1.51 \lg z\right)1.51 \lg z}}{150 + 300c}$$

$k\text{-value} = 1000k$

Here in it was defined:

$$Z = \frac{t_c}{t_0} = \frac{\eta_c}{\eta_0} \text{ relative Viscosity,}$$

$\eta_c$ dynamic viscosity of the solution,
$\eta_0$ dynamic viscosity of the solvent and
c mass concentration of polymer in solution in in g/cm$^3$.

Alternatively the k-value can be evaluated from lists provided by the manufacturer of the equipment.

After determination of the mass concentration of the polymer solution by microwave drying with a CEM Smart 5 at 120° C., 20 ml of a 0.5% polymer solution was prepared. 16 to 18 ml of the solution was measured in an Ubbelhode capillary viscometer at 25° C. The Ubbelhode viscometer was chose to have a pass-through time of 100 to 120 s. It was measured in a Schott AVS viscometer, combined with a CT 1150 Thermostate and flow cooler CK 100.

The IT unit calculated the k-value.
Brookfield viscosity in 1% solution:
Brookfield viscosity was determined with a Brookfield viscometer model LV, RVT DV-II or LVT DV-II.

In a 600 ml beaker, 4 g dry Polymer was dissolved in 394 g distilled water. The solution was stirred for 2 h at 20° C. with a finger stirrer driven by an overhead agitator at 200 rpm. Then the polymer solution, free of entrapped air, was tempered for 16 h at 20° C. The spindle was chosen to measure between 20 to 80% of the scale at 20 rpm.

Brookfield viscosity in solution as is.
Brookfield viscosity was determined with a Brookfield viscometer model LV, RVT DV-II or LVT DV-II.

In a 600 ml beaker, the polymer solution, free of entrapped air, was tempered for 2 h at 20° C. The spindle was chosen to measure between 20 to 80% of the scale at 20 rpm.

Analytical procedure for determination of bio-based content according to ASTM 6866-12, Method B:

The provided sample material did not undergo any pretreatment procedure and was converted to graphite as was using the following procedure.

Depending on the estimated amount of carbon content, typically a few milligram of sample material was being combusted in an Elemental Analyzer (EA). The resulting gas mixture was being cleaned and $CO_2$ was automatically separated by the EA using the purge and trap technology.

The remaining $CO_2$ was transferred into a custom-made graphitization system, converted into carbon (graphite) catalytically using $H_2$ and an iron-powder catalyst. The carbon-14 determination of the graphite was performed at the Klaus-Tschira-Archaeomtrie-Center using an accelerator mass-spectrometer (AMS) of the type MICADAS (developed at the ETH Zurich, Switzerland).

What is claimed is:

1. A compound according to Formula (3), wherein the compound comprises from 28 wt. % to 100 wt. %, bio-based carbon content, relative to the total mass of carbon in the compound, according to standard ASTM D6866-12, Method B, calculated by multiplying the percent modern carbon value, as determined by measuring the carbon-14 content relative to the total carbon content, by a correction factor of 0.95;

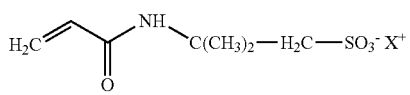
(3)

and wherein $X^+$ is a proton.

2. A compound, according to Formula (3), derived from isobutene, wherein the isobutene has at least 90 wt. % bio-based carbon content, relative to the total mass of carbon in isobutene, according to standard ASTM D6866-12, Method B, calculated by multiplying the percent modern carbon value, as determined by measuring the carbon-14 content relative to the total carbon content, by a correction factor of 0.95;

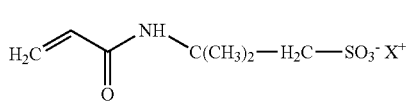
(3)

and wherein $X^+$ is a proton.

3. A compound, according to Formula (3), derived from acrylonitrile, wherein the acrylonitrile has at least 90 wt. % bio-based carbon content, relative to the total mass of carbon in acrylonitrile, according to standard ASTM D6866-12, Method B, calculated by multiplying the percent modern carbon value, as determined by measuring the carbon-14 content relative to the total carbon content, by a correction factor of 0.95;

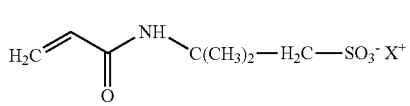
(3)

and wherein $X^+$ is a proton.

4. The compound according to claim 1, wherein the compound is derived from both isobutene and acrylonitrile, wherein the isobutene has at least 90 wt. % bio-based carbon content, relative to the total mass of carbon in isobutene, measured according to standard ASTM D6866-12, Method B, calculated by multiplying the percent modern carbon value, as determined by measuring the carbon-14 content relative to the total carbon content, by a correction factor of 0.95; and wherein the acrylonitrile has at least 90 wt. % bio-based carbon content, relative to the total mass of carbon in acrylonitrile, measured according to standard ASTM D6866-12, Method B.

5. A polymer prepared by polymerising at least one compound according to Formula (3), wherein the at least one compound according to Formula (3) comprises from 28 wt. % to 100 wt. %, bio-based carbon content, relative to the total mass of carbon in the compound, according to standard ASTM D6866-12, Method B, calculated by multiplying the percent modern carbon value, as determined by measuring the carbon-14 content relative to the total carbon content, by a correction factor of 0.95;

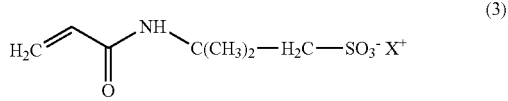

and wherein X⁺ is a proton.

6. A polymer according to claim 5, wherein the polymer comprises at least one repeating unit according to Formula (1),

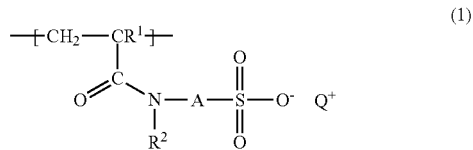

wherein $R^1$ and $R^2$ are H; A is —C(CH$_3$)$_2$—H$_2$C—; and Q+ is cation.

7. The polymer according to claim 5, wherein the polymer has a weight average molecular weight of at least 700 g/mol.

8. The polymer according to claim 5, wherein the polymer is a homopolymer.

9. A process for synthesizing a compound according to Formula (3), comprising reacting acrylonitrile, fuming sulfuric acid and isobutene in a solvent; wherein the isobutene has at least 90 wt. % bio-based carbon content, relative to the total mass of carbon in isobutene, measured according to standard ASTM D6866-12, Method B, calculated by multiplying the percent modern carbon value, as determined by measuring the carbon-14 content relative to the total carbon content, by a correction factor of 0.95;
and/or wherein the acrylonitrile has at least 90 wt. % bio-based carbon content, relative to the total mass of carbon in acrylonitrile, measured according to standard ASTM D6866-12, Method B, calculated by multiplying the percent modern carbon value, as determined by measuring the carbon-14 content relative to the total carbon content, by a correction factor of 0.95;

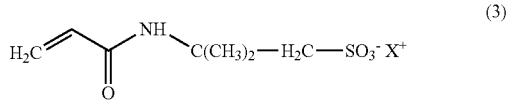

and wherein X⁺ is a proton.

10. The process according to claim 9, comprising:
(a) a first step of mixing fuming sulfuric acid with the acrylonitrile to produce a mixture of acrylonitrile and fuming sulfuric acid in an aprotic polar solvent;
(b) a second step of contacting the mixture produced in the first step, with the isobutene, to obtain an aprotic polar solvent slurry of compound according to Formula (3)

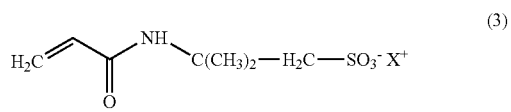

wherein X⁺ is a proton;
(c) optionally a third step of subjecting the slurry obtained in the second step, to solid-liquid separation to obtain a cake of crude compound according to Formula (3), and then washing the cake with an aprotic polar solvent of mass of at least two times that of the cake, and
(d) optionally a fourth step of drying the cake washed in the third step.

11. The process according to claim 10, wherein the first step is carried out at a temperature of from −50° C. to 10° C.

12. The process according to claim 10, wherein the second step is carried out at a temperature of from 10° C. to 70° C.

13. The process according to claim 9, further comprising isolating a compound according to Formula (3);

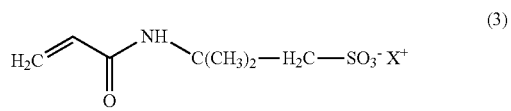

wherein X⁺ is a proton; and then optionally employing said compound to synthesize a polymer.

14. A polymer according to claim 5, wherein the at least one compound according to Formula (3) is derived from isobutene, wherein the isobutene has at least 90 wt. % bio-based carbon content, relative to the total mass of carbon in isobutene, according to standard ASTM D6866-12, Method B, calculated by multiplying the percent modern carbon value, as determined by measuring the carbon-14 content relative to the total carbon content, by a correction factor of 0.95.

15. A polymer according to claim 5, wherein the at least one compound according to Formula (3) is derived from acrylonitrile, wherein the acrylonitrile has at least 90 wt. % bio-based carbon content, relative to the total mass of carbon in acrylonitrile, according to standard ASTM D6866-12, Method B, calculated by multiplying the percent modern carbon value, as determined by measuring the carbon-14 content relative to the total carbon content, by a correction factor of 0.95.

16. A polymer according to claim 5, wherein the at least one compound according to Formula (3) is derived from both isobutene and acrylonitrile, wherein the isobutene has at least 90 wt. % bio-based carbon content, relative to the total mass of carbon in isobutene, measured according to standard ASTM D6866-12, Method B, calculated by multiplying the percent modern carbon value, as determined by measuring the carbon-14 content relative to the total carbon content, by a correction factor of 0.95; and wherein the acrylonitrile has at least 90 wt. % bio-based carbon content, relative to the total mass of carbon in acrylonitrile, measured according to standard ASTM D6866-12, Method B, calculated by multiplying the percent modern carbon value, as determined by measuring the carbon-14 content relative to the total carbon content, by a correction factor of 0.95.

17. A compound according to claim 2, made by a process comprising reacting acrylonitrile, fuming sulfuric acid and isobutene in a solvent; wherein the isobutene has at least 90 wt. % bio-based carbon content, relative to the total mass of carbon in isobutene, measured according to standard ASTM D6866-12, Method B, calculated by multiplying the percent modern carbon value, as determined by measuring the carbon-14 content relative to the total carbon content, by a correction factor of 0.95.

18. The compound of claim 17, wherein the acrylonitrile has at least 90 wt. % bio-based carbon content, relative to the total mass of carbon in acrylonitrile, measured according to standard ASTM D6866-12, Method B, calculated by multiplying the percent modern carbon value, as determined by measuring the carbon-14 content relative to the total carbon content, by a correction factor of 0.95.

19. The process of claim 9, wherein the isobutene has at least 90 wt. % bio-based carbon content, relative to the total mass of carbon in isobutene, measured according to standard ASTM D6866-12, Method B, calculated by multiplying the percent modern carbon value, as determined by measuring the carbon-14 content relative to the total carbon content, by a correction factor of 0.95.

20. The process of claim 9, wherein the acrylonitrile has at least 90 wt. % bio-based carbon content, relative to the total mass of carbon in acrylonitrile, measured according to standard ASTM D6866-12, Method B, calculated by multiplying the percent modern carbon value, as determined by measuring the carbon-14 content relative to the total carbon content, by a correction factor of 0.95.

\* \* \* \* \*